United States Patent
De Freitas Nascimento et al.

(10) Patent No.: US 11,300,690 B2
(45) Date of Patent: Apr. 12, 2022

(54) DETERMINATION OF RADIATION DOSIMETRY

(71) Applicant: SCK-CEN, Brussels (BE)

(72) Inventors: Luana De Freitas Nascimento, Antwerp (BE); Filip Vanhavere, Antwerp (BE); Lara Struelens, Aarschot (BE); Mark Akselrod, Stillwater, OK (US)

(73) Assignee: SCK-CEN, Brussels (BE)

(*) Notice: Subject to any disclaimer, the term of this patent is extended or adjusted under 35 U.S.C. 154(b) by 0 days.

(21) Appl. No.: 16/683,444

(22) Filed: Nov. 14, 2019

(65) Prior Publication Data
US 2020/0158889 A1 May 21, 2020

(30) Foreign Application Priority Data
Nov. 16, 2018 (EP) .................................... 18206873

(51) Int. Cl.
*G01T 1/29* (2006.01)
*G01T 1/02* (2006.01)
*A61N 5/10* (2006.01)

(52) U.S. Cl.
CPC ............ *G01T 1/023* (2013.01); *A61N 5/1075* (2013.01)

(58) Field of Classification Search
CPC ......... G01T 1/023; G01T 1/29; A61N 5/1048; A61N 5/1071; A61N 5/1075
See application file for complete search history.

(56) References Cited

U.S. PATENT DOCUMENTS

| 2007/0181815 | A1* | 8/2007 | Ebstein | G01T 1/02 250/370.11 |
| 2012/0168630 | A1* | 7/2012 | Beddar | G01T 1/04 250/362 |
| 2015/0360056 | A1* | 12/2015 | Xing | A61N 5/1075 600/1 |
| 2017/0326387 | A1* | 11/2017 | D'Agostino | A61N 5/1071 |

FOREIGN PATENT DOCUMENTS

| WO | 2016083473 A1 | 6/2016 |
| WO | 2018124874 A1 | 7/2018 |

OTHER PUBLICATIONS

Extended European Search Report from corresponding EP Application No. 18206873.4, dated Mar. 29, 2019.

* cited by examiner

*Primary Examiner* — David P Porta
*Assistant Examiner* — Fani Boosalis
(74) *Attorney, Agent, or Firm* — Workman Nydegger

(57) ABSTRACT

The present invention describes a dosimetry system for use in an irradiation system for radiology or radiotherapy. The dosimetry system comprises an at least two dimensional, radioluminescent, irradiation detection surface comprising radiosensitive material, the radiosensitive material having radioluminescent properties. The system also comprises a detection system configured for detecting radioluminescent radiation from the at least two-dimensional detection surface upon irradiation with a radiology or radiotherapy irradiating beam. The detection system comprises a detector sensitive for radioluminescence and a filter for at least partially blocking radiation from said radiology or radiotherapy irradiating beam and ambient light.

19 Claims, 2 Drawing Sheets

DETERMINATION OF RADIATION DOSIMETRY

FIELD OF THE INVENTION

The invention relates to the field of radiation dosimetry. More specifically it relates to methods and systems for performing two-dimensional real-time dosimetry in radiation beam applications (radiology or radiotherapy), e.g. in medical radiation beam applications.

BACKGROUND OF THE INVENTION

Radiation quality control measurements are very important in medical applications like radiotherapy, diagnostic and interventional radiology, etc. In case of radiotherapy, the equilibrium between the necessary dosage for a successful treatment (increasing 'tumor control probability', TCP) and the dosage harming normal tissue (decreasing 'normal tissue complication probability', NTCP) is very delicate. It requires the utmost careful and precise control of the applied dose, the area of the radiated region, the number and frequency of doses, the energy of radiation, etc. In this regard, the radiotherapeutic technology has advanced considerably with the aim to deliver higher doses of radiation to the tumor and lower doses to the surrounding tissue. For example, intensity-modulated radiotherapy (IMRT) aims to deliver conformal doses to the tumor while minimizing the dose to surrounding normal critical structures. Another example is proton-beam radiotherapy (PT) which reduces the dose to adjacent normal tissues. Nonetheless the increased complexity of these techniques adds a degree of uncertainties to the delivered dose.

The current clinical protocol to know the delivered dose to the tumor and to the surrounding organs is through the treatment planning systems (TPS) which uses mathematical algorithms. However due to errors in for example positioning of the patient a precise dose calculation does not always correspond to the actual dose delivered to the patient. These errors and other uncertainties, such as radiation scattering, result in the fact that the doses from the TPS do not always provide the accurate doses to the patient. The development of procedures for real-time in vivo dosimetry in radiotherapy forms an important task (IAEA, Human Health Reports No. 8, Vienna 2013).

In vivo dosimetry techniques currently involve electronic portal imaging devices (EPIDs), placed behind the patient to image the exit doses, and point source measurements by applying detectors such as for example thermoluminescence detectors (TLDs) or diodes on the skin or immobilization devices of patients. This protocol includes the measurement of entrance and exit doses directly on the patient and to perform a direct quality assurance of radiotherapy. However, these techniques are not applicable to IMRT or treatment with very small fields and remains a laborious technique. Moreover, EPIDs are not suitable for proton and hadron therapy beams, once there is not exit dose, while in the case of point detectors, these techniques do not deliver two-dimensional information on the dose distribution and its repeatability (positioning the detectors on exactly the same position on the patient) is uncertain.

Due to the fact that most treatments comprise periodical measurements during weeks or months, specific immobilization elements are used in most of the treatment protocols. Examples of these elements include vacuum-lock cushions, "belly boards", and for good reproducibility during a long-term treatment, immobilization molds (perspex shells or other thermoplastic molds). In case of cerebral tumor irradiation for example masks are fixated and molded to enable control of the localization of the provided radiation in subsequent treatments.

International patent application WO2016/083473 describes a mask for immobilization of a region of interest during radiation therapy. The mask is adapted for partially storing the radiation energy in radiation-sensitive material in those regions exposed to the radiation during radiation therapy. The document also discloses a method for obtaining radiation therapy doses estimation, by collecting a physical response of the radiation-sensitive material over the surface of the mask upon stimulation. Both optically stimulated luminescence (OSL) and radiophotoluminescence (RPL) are described. Both in-situ measurement during irradiation therapy and off-line dosimetry are suggested for, but the methods described are especially suitable for passive, post-irradiation total absorbed dose assessment.

Nevertheless, there is still room for improvement for performing real-time, online, in-situ dosimetry since the currently available methods and systems are complex.

SUMMARY OF THE INVENTION

It is an object of embodiments of the present invention to provide methods and systems for performing accurate in-situ two-dimensional dosimetry during radiology or radiotherapy.

It is an advantage of embodiments of the present invention that methods and systems are provided that allow for accurate, online, in-situ two-dimensional dosimetry whereby an immediate feedback (millisecond) to the dose and dose rate from a radiology or radiotherapy system is obtained.

It is an advantage of embodiments of the present invention that methods and systems are provided that do not require optical stimulation for obtaining dosimetry, rendering the methods and systems for dosimetry less complex.

The above objective is accomplished by a method and device according to the present invention.

In a first aspect, the present invention relates to a dosimetry system for use in an irradiation system for radiology or radiotherapy, the dosimetry system comprising an at least two dimensional, radioluminescent, irradiation detection surface comprising radiosensitive material, the radiosensitive material having radioluminescent properties, a detection system configured for detecting radioluminescent light from the at least two-dimensional detection surface upon irradiation with a radiology or radiotherapy irradiating beam, the detection system comprising a detector sensitive for radioluminescence and a filter for at least partially blocking radiation from said radiology or radiotherapy irradiating beam and ambient light.

It is an advantage of embodiments of the present invention that accurate doses detection of radiology or radiotherapy irradiation can be performed by detecting radioluminescent light from a radioluminescent, irradiated surface. It is an advantage of embodiments of the present invention that the detection system is adapted for filtering out at least partially radiation from the radiology or radiotherapy irradiating beam and for filtering out at least partially ambient light, so that accurate detection of radioluminescent light with a good signal to noise ratio can be detected.

The at least two dimensional, radioluminescent, irradiation detection surface may be adapted for emitting a radioluminescent signal upon being irradiated with the radiology or radiotherapy irradiation beam, without the need for a further external stimulus. It is an advantage of embodiments of the present invention that no external stimulus such as for example temperature or further radiation is required.

The radiosensitive material may have an emission decay time between 1 ns and 100 ms. The filter may be adapted for blocking ambient radiation, room light and/or any contaminating light in a wavelength range between 10 nm and 700 nm.

The filter may be any of a bandpass filter, a long pass filter, a short pass filter, a notch filter, a dichroic filter, an imaging filter or a neutral density filter.

The detector may be adapted for detecting light in any predetermined angle of incidence.

The dosimetry system may furthermore comprise a processor for processing the detected radioluminescence signals and for calculating based thereon a relative or organ doses of irradiation and/or a position thereof provided to the object.

The dosimetry system may comprise a controller for controlling the detection of radioluminescence so that it happens online during the radiology or radiotherapy.

The controller may furthermore be adapted for adjusting the radiology or radiotherapy system based on a determined dose and/or position of the detected irradiation.

The radiation-sensitive material may be an organic or inorganic luminescent material suitable for radioluminescence (RL) and scintillation. It is an advantage of embodiments of the present invention that the radiation-sensitive material furthermore comprises a material sensitive for scintillation. It is an advantage of embodiments of the present invention that the radiation-sensitive material comprises inorganic scintillators such as for example $BaF_2$, $CaF_2(Eu)$, $ZnS(Ag)$, $CaWO_4$, $CdWO_4$, $YAG(Ce)$, $NaI(Tl)$, LYSO, BGO, $CsI(Tl)$, $CsI(Na)$, insulators such as for example BeO, LiF, $Al_2O_3$:C, $Al_2O_3$:C,Mg, plastics such as for example Polyethylene naphthalate, fluors such as for example n-terphenyl or glasses.

The radiation-sensitive material may be sensitive to ionizing radiation being one or more of γ radiation, β radiation, α radiation, X-rays, protons radiation beams, hadrons radiation beams and neutrons radiation beams.

It is an advantage of embodiments of the present invention that the system is making use of a camera as detector that measures exposure over the whole body of the patient, and that generates 2-D radiation exposure data, e.g. real-time 2-D radiation exposure data. By using a camera or detector comprising a plurality of pixels for forming an image, one can gather information from the patient, because it does not only visualize the radio luminescence coming from the detection surface comprising radiosensitive material having radioluminescent properties, but it also visualizes radioluminescence coming from everything in the environment, such as for example from the patient. By using a camera, distinction can be made between the radio luminescence coming from the detection surface and radio luminescence coming from the environment, thus allowing a more accurate detection.

In some embodiments, the dosimetry system thus may be configured for taking into account whether radio luminescence stems from the radiosensitive material having radioluminescent properties or from the environment. The environment thereby may be all elements different from the sensitive material, and thus may for example include the patient. The dosimetry system may have a controller allowing, based on the detection of radioluminescence performed, distinguishing whether radioluminescence stems from the radiosensitive material or the environment. The controller may communicate with the processor for taking the origin of the radioluminescence into account when processing the detected radioluminescence signals and when calculating based thereon a relative or organ doses of irradiation and/or a position thereof provided to the object.

It is an advantage of embodiments of the present invention that by using radio luminescent material, a previously stored signal can be easily set back to zero, since detection does not need to be based on a cumulative result. The latter may assist in obtaining a good dynamic range. Using radioluminescence, the dynamic range may be from a few microGy to 100 Gy.

The present invention also relates to an irradiation system comprising a dosimetry system as described above.

The detection system for detecting radioluminescence may be positioned substantially facing or parallel to an irradiation source of the irradiation system.

The present invention furthermore relates to a method for determining irradiation doses during radiology or radiotherapy for an object, the method comprising providing an at least two dimensional, radioluminescent, irradiation detection surface on the object, detecting radioluminescent signals from the at least two dimensional, radioluminescent irradiation detection surface, while filtering out ambient light and radiation stemming from the irradiation beam for performing radiology or radiotherapy, and deriving a delivered dose and/or irradiation position on the object based on the detected radioluminescent signals.

It is an advantage of embodiments of the present invention that use is made of the radioluminescence phenomenon, whereby no external stimulation is required for reading out a physical response of radiation-sensitive material to an irradiation dose.

It is an advantage of embodiments of the present invention that good methods and systems are provided for determining entrance skin dose rate, time resolved absorbed dose and beam position/distribution during radiation therapy. It is an advantage of embodiments of the present invention that the systems and/or methods are especially suitable for dosimetry during radiology or radiotherapy.

It is an advantage of embodiments of the present invention, that use is made of a 2D matrix or surface (e.g, immobilization element/medical sheet/medical tissue/patch/mask) that is positioned over the skin of the patient, thus allowing accurate determination of the entrance skin dose rate and beam 2D position on the patient.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
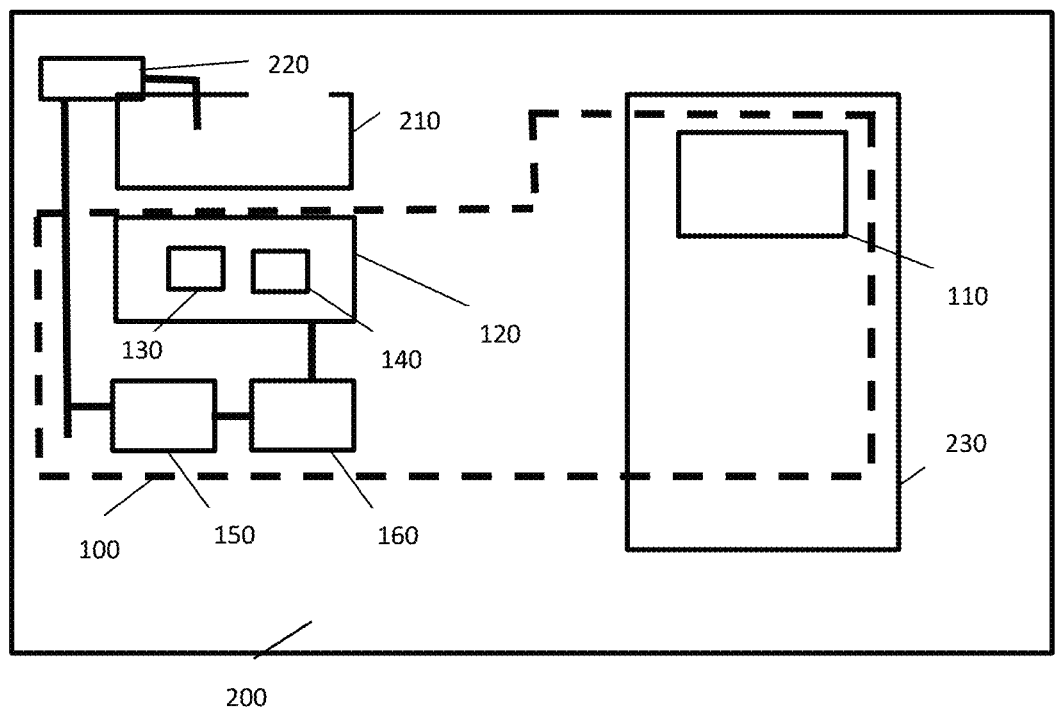
FIG. 1 illustrates a schematic representation of a dosimetry system and a radiotherapy system according to embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some, but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to radioluminescence, reference is made to the radiation produced proportional to a beam dose rate of x-rays, electrons, protons or heavy ions with which the radioluminescent material is irradiated.

Where in embodiments of the present invention reference is made to "2D matrix", reference is made to a shaped membrane with such elastic properties that allow tight fixation or folding towards different forms. The membrane may comprise thermoplastics or other polymers, although the present invention is not limited thereto. Likewise, the term "2D matrix" is not limiting to its use, the matrix being applicable to any region, volume or object. The shape of the membrane is advantageously optimized for each particular matrix application and advantageously is two-dimensional, following the boundaries of the object around the region of interest. In some embodiments of the present invention, the matrix may be suitable for example for immobilization of head, or extremities, or any other part of a body, not being limited thereto, or it may be used for molding, not being limited thereto.

In a first aspect, the present invention relates to a dosimetry system for use in an irradiation system for both diagnosis and treatment (e.g., radiology, radiotherapy). The dosimetry system according to embodiments of the present invention advantageously allows online dosimetry determination during irradiation. It allows in vivo dosimetry. It may be especially suitable for performing dosimetry when performing radiology or radiotherapy on living creatures, such as for example human beings. According to embodiments of the present invention, the dosimetry system comprises an at least two dimensional, radioluminescent, irradiation detection surface comprising radiosensitive material. The two-dimensional irradiation detection surface can provide information regarding the position of where the irradiation beam enters the skin as well as the dose in real time of irradiation that is received at different positions of the surface. According to embodiments of the present invention, the radiosensitive material has radioluminescent properties.

The system furthermore comprises a detection system configured for detecting radioluminescent light from the at least two dimensional, radioluminescent, irradiation detection surface upon irradiation with a radiology or radiotherapy irradiating beam. The detection system comprises a detector sensitive for radioluminescence light and a filter for at least partially blocking radiation from said radiology or radiotherapy irradiating beam and ambient light.

By way of illustration, embodiments of the present invention not being limited thereto, an example of a method and system according to an exemplary embodiment is further discussed below.

An exemplary system is illustrated in FIG. 1, schematically illustrating the different components of a dosimetry system according to embodiments of the present invention. The dosimetry system 100 comprises an at least two dimensional, radioluminescent, irradiation detection surface 110.

The two-dimensional, radioluminescent, irradiation detection surface 110, advantageously is adapted for detecting, i.e. being responsive to, one or more ionizing radiation types, such as for example one or more of γ radiation, β radiation, ε radiation, X-rays, protons radiation beams, hadrons radiation beams and neutrons radiation beams. The irradiation detection surface 110 may be a two dimensional or a three-dimensional surface. Advantageously, the detection surface extends mainly in two directions and has a limited thickness. It may for example be a membrane. The irradiation detection surface 110 may be a membrane shaped surface having a thickness between 1 μm and 10 mm, e.g. between 2 μm and 5 mm. The irradiation detection surface 110 may have a surface area between 1 mm$^2$ and 10000 cm$^2$, e.g. between 10 mm$^2$ and 2500 cm$^2$.

The irradiation detection surface 110 may be flexible and shapeable according to the part of the body it is covering. Alternatively, it may be more rigid and shaped according to the part of the body it is intended to cover. The irradiation detection surface 110 may have a hardness between Shore 00 (rubbers and gels that are very soft) and Shore D (hard rubbers, semi-rigid plastics and hard plastics) on the Shore Hardness scales. According to some embodiments, the irradiation detection surface 110 may at the same time also be an immobilization device, e.g. an immobilization device for a body part. It is to be noticed that such an immobilization device is not restricted to a face mask, but alternatively may be suitable for masking another bodily part, such as for example a limb, an abdomen, a thorax, etc. The irradiation detection surface may be as described in international patent application WO2016/083473, but whereby the radiation-sensitive material comprises radioluminescence properties, as described below.

The irradiation detection surface 110 according to embodiments of the present invention typically comprises radiation-sensitive material comprising radioluminescent properties. The radiation-sensitive material may comprise powdered materials. The powdered materials may be micro-sized, e.g. have an average diameter between 1 μm and 1000 μm, or nano-sized, e.g. having an average diameter between 1 nm and 1000 nm. The radiation-sensitive material may be dispersed substantially homogeneously in or over the irradiation detection surface 110. The radiation-sensitive material may be an organic or an inorganic luminescent material. In some embodiments, aside from the radioluminescent properties, the radiation-sensitive material or part thereof also may comprise scintillation properties. The radiation-sensitive material may for example comprise inorganic scintillators such as for example BaF$_2$, CaF$_2$(Eu), ZnS(Ag), CaWO$_4$, CdWO$_4$, YAG(Ce), NaI(Tl), LYSO, BGO, CsI(Tl), CsI(Na), insulators such as for example BeO, LiF, Al$_2$O$_3$:C, Al$_2$O$_3$:C,Mg, plastics such as for example Polyethylene naphthalate, fluors such as for example n-terphenyl or glasses. In some embodiments, the radiation-sensitive material may comprise a single type of luminescent material. In some embodiments of the present invention, the radiation-sensitive material may comprise a combination of several luminescence materials. Not all of these need to be radioluminescent, but at least some of them need to be radioluminescent.

It is an advantage of embodiments of the present invention that no external stimulation needs to be provided for the irradiation detection surface to emit radiation representative of information regarding position and/or dose of the radiology or radiotherapy irradiation that was applied, but that the emission is spontaneous. This is in contrast to for example systems based on optically stimulated luminescence, thermoluminescence, radiophotoluminescence, etc.

The radiation-sensitive material may be emitting its radioluminescence in one or more specific wavelengths. Some examples are Al$_2$O$_3$:C emitting substantially at 420 nm, BaF$_2$ emitting substantially at 310 nm and at 295 nm, Gd$_2$O$_2$S:Tb emitting at 545 nm. The radiation-sensitive material emits light that changes in intensity depending on the incident ionizing irradiation intensity, and therefore the emitted light is a representation for the dose-rate. The radiation-sensitive material may emit light with a half-life in the range of a few ns to s. The radiation-sensitive material may emit radiation with a half-life and dynamic range from or a few gtGy/min to MGy/min.

As indicated above, the dosimetry system 100 also comprises a detection system 120 configured for detecting radioluminescent light from the at least two dimensional, radioluminescent, irradiation detection surface 110 upon irradiation with an irradiating beam. The detection system 120 comprises a detector 130 sensitive for radioluminescence light from the irradiation detection surface 110. The detector 130 may be a camera sensor, being a solid-state device, which captures the radioluminescence light to form a digital image. The detector typically is sensitive to visible and/or UV light, with a dynamic range. The detector typically will be matched to the expected radioluminescence light spectrum, depending on the irradiation detection surface used. The detector 130 thus may have a high quantum efficiency for the wavelengths at which the irradiation detection surface 110 emits its radioluminescence. It may have an adjustable frequency, e.g. adjustable in the range 1000 to 1 Hz. The detector 130 may be any of a CCD, EMCCD, CMOS, LiveMOS, InGaAs SWIR, SWIR, TDI CCD and/or OEM detector. The detector 130 may have a size ranging from full frame (36 mm×24 mm) to smaller sizes, e.g. 1×1 mm. The detector typically has a plurality of pixels wherein each pixel contains one or more light sensitive photodetection elements. The detector 130 may be monochrome or colour. The detector may have a video output which may be PAL, NTSC, ITU-R, BT.656-4 compatible. The detector alternatively or in addition thereto may have a digital output, which may be compatible with CameraLink, GigE, LVDS, USB.

The detection system also comprises a filter 140 for at least partially blocking radiation from said radiology or radiotherapy irradiating beam and ambient light. The filter may have a size, shape and thickness such that it fits the detector 130. The filter 140 may selectively transmit or reject a wavelength or range or combination of wavelengths. The filter 140 typically may transmit radiation of the wavelength corresponding with the radioluminescence emitted by the matrix. The filter may be blocking ambient light, e.g. room light, in a wavelength range between 10 and 800 nm.

It may have a center wavelength (CWL) ranging between 5 nm and 400 nm. The filter 140 may be coated or not. It may have a metallic based coating. It may have hard coatings with high optical densities. It may be composed of one or a combination of glasses. In some embodiments, the filter may belong to a specific category of filters, such as for example a bandpass filter, a long pass filter, a short pass filter, a notch filter, a dichroic filter, an imaging filter, a neutral density filter, etc. The filter may be an optical density filter, whereby the optical density may vary from 0.3 to 10. The optical filter may in some embodiments be a passband filter, wherein, when the filter is installed, at least 93% of the radiation is transmitted to the detector in a narrow wavelength band and wherein outside the passband, radiation is blocked with an optical density of at least 6.

According to embodiments of the present invention, the filter 140 or a separate filter may be adapted so as to transmit only radiation having an angle of incidence within a predetermined range. Such a range may be narrow and may for example be within 10° of a predetermined angle of incidence, e.g. within 5° of a predetermined angle of incidence.

Figure 2:
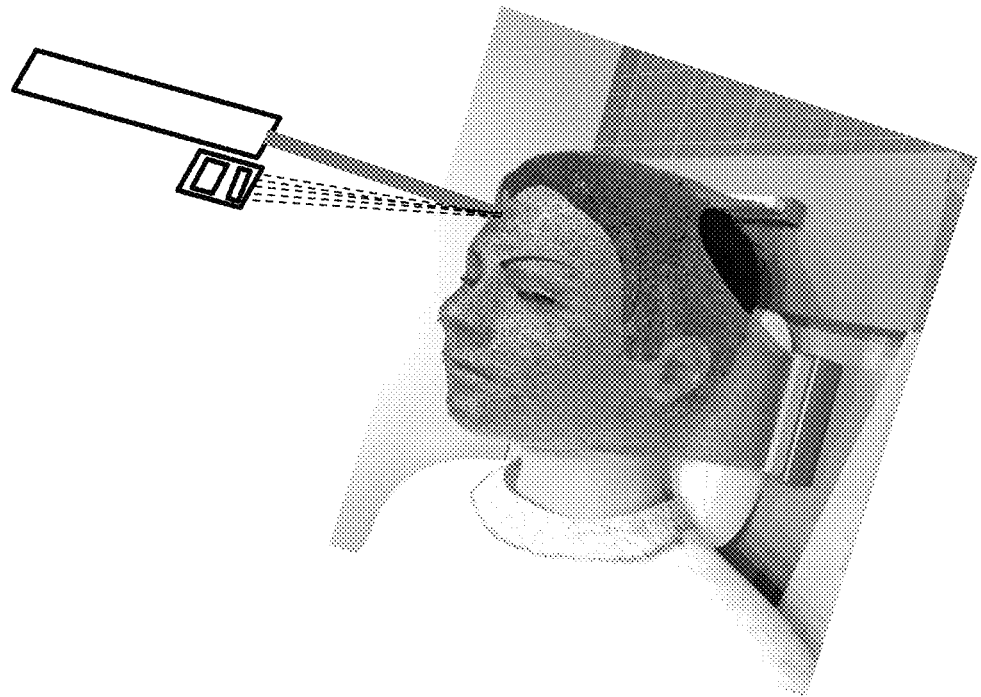
FIG. 2 show a system according to embodiments of the present invention, whereby a scientific camera collects real time emitted light from radioluminescence materials when exposed to ionizing radiation.

According to embodiments of the present invention, the detection system will be positioned adjacent to the radiation source, e.g. parallel to it, such that due to the configuration the amount of radiation stemming directly from the irradiation source is as small as possible. The latter is illustrated in FIG. 2.

According to some embodiments, the system 100 also comprises a controller 150 for controlling the detection of radioluminescence and thus for controlling the doses detection. The controller on the one hand may control the timing of detection and doses determination. The controller on the other hand may adjust the radiology or radiotherapy system, e.g. a treatment planning device thereof, to adjust in real-time or for future treatment purposes, the irradiation during radiology or radiotherapy. For example, when a predetermined dose and/or dose rate is reached, the irradiation can be stopped or can be altered. When a dose is measured at a position where no irradiation should occur, the system may be stopped, and repositioning of the object may be performed. The controller may be programmed for comparing the detected doses with the dose planned by the treatment planning system and may adjust the therapy based thereon.

According to some embodiments, the system 100 also comprises a processor 160 for processing the detected signals and calculate based thereon relative or effective doses of irradiation provided to the object, e.g. patient. The processor 160 may be a separate processor or integrated in another part of the system.

The algorithms performed may be programmed in software or hardware.

In another aspect, the present invention relates to an image radiology or radiotherapy system for irradiating an object. The image radiology or radiotherapy system comprises a dosimetry system as described in the first aspect. The radiology or radiotherapy system furthermore comprises conventional elements as known by the person skilled in the art, such as for example an irradiation source, an irradiation therapy planning system, a positioning system for positioning the object, etc. Features and advantages may be as mentioned in the first aspect. The image radiology or radiotherapy system 200 is shown in FIG. 1, illustrating the irradiation source 210, the irradiation therapy planning system 220 and the positioning system 230 for positioning the object In yet another aspect, the present invention relates to a method for determining irradiation doses during radiology or radiotherapy for an object, e.g. a patient.

The method comprises providing an at least two dimensional, radioluminescent, irradiation detection surface on a patient, detecting radioluminescent signals from the at least two dimensional, radioluminescent irradiation detection surface, while filtering out ambient radiation and radiation stemming from the irradiation beam for performing radiotherapy (and/or radiology), and deriving a delivered dose and/or irradiation position on the object based on the detected radioluminescent signals. The 2D dose can be further reconstructed to the 3D dose delivered to the patient. Further steps may correspond with the functionalities of the components described in the first aspect.

The present invention furthermore relates to the use of a dosimetry system as described in the first aspect for dosimetry during irradiation of an object, e.g. a patient. The present invention also relates to the use of a dosimetry system as described in the first aspect during subsequent irradiation sessions for radiotherapy or radiology. The present invention furthermore relates to the use of a dosimetry system as described in the first aspect for controlling dosis delivered to an object or for treatment planning verification for radiology or radiotherapy.

In one example, illustrating features and advantages of at least some embodiments of the present invention, a method and system is described for assessing the two-dimensional real-time amount of ionizing radiation a patient receives when undergoing a radiology or radiotherapy treatment. It is based on real time recording of the light emission from a 2D sheet composed of a radioluminescent (RL) material (e.g. $Lu_3Al_5O_{12}$:Pr, BeO, ZnO, $Al_2O_3$:C, $Al_2O_3$:C,Mg, $CaF_2$:Th, alkali halide crystals), which under irradiation generates free electron-holes that promptly recombine in recombination centres. The emitting light is proportional to the ionizing radiation dose rate. The RL light is collected/measured by a scientific camera (CCD, sCMOS, CMOS, CMOSIS, InGaAs, EMCCD, and Semiconductor) in combination with short-pass/band-pass filters to limit the detection to the main emission coming from the RL 2D sheet. Camera and filters are placed parallel to the head of the LINAC (linear accelerator) or proton/hadron therapy beam, out of the main radiation field, facing the patient perpendicularly, or at any desired angle.

The 2D radioluminescent sheet covers the skin of patients undergoing radiology or radiotherapy treatment. The camera is in the example also perpendicular to the 2D sheet. For static (conventional) and dynamic treatments (IMRT, rapidArc, VMAT, pencil beam) the camera is capable of imaging the changes in shape and intensity of ionizing radiation striking the 2D sheet, and consequently, the skin of the patient, providing a real-time in vivo dosimetry tool for patient safety.

A dedicated automated software analyzes the measured data and compares it with the treatment planning system for routine in vivo dosimetry (IVD) in the clinical workflow. The software uses the information from each of the treatment fields (beams or arcs) and the intensities (dose-rate) planned in the TPS, and compares this information with the delivered treatment. The system allows to comply with dosimetry requirements and QA during the treatment delivery and verification process.

Figure 3A:
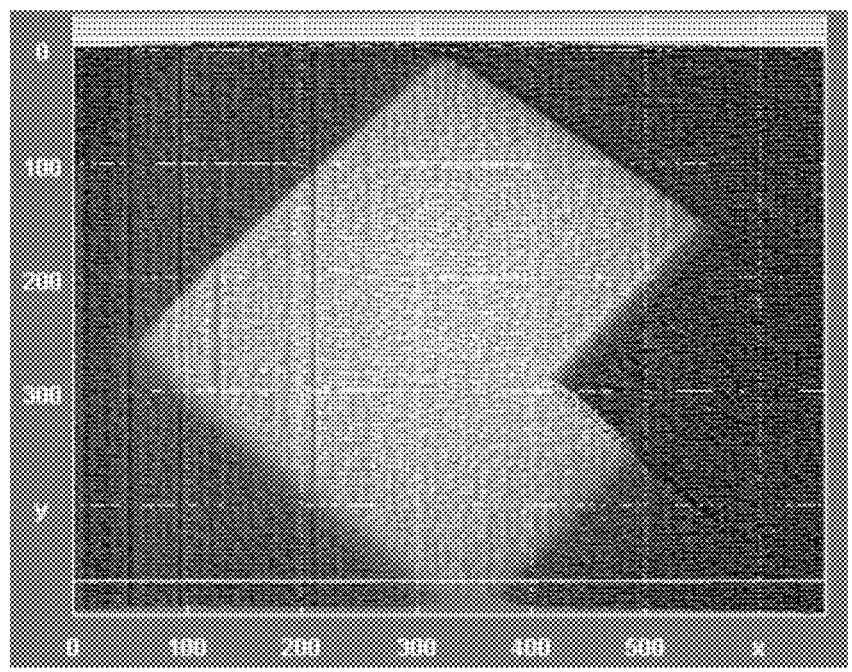
FIG. 3a and FIG. 3b shows a 2D and 3D representation of radioluminescent (RL) light emitted in real time from an Al2O3:C,Mg sheet, acquired with an EMCCD camera, illustrating features of embodiments of the present invention.
Figure 3B:
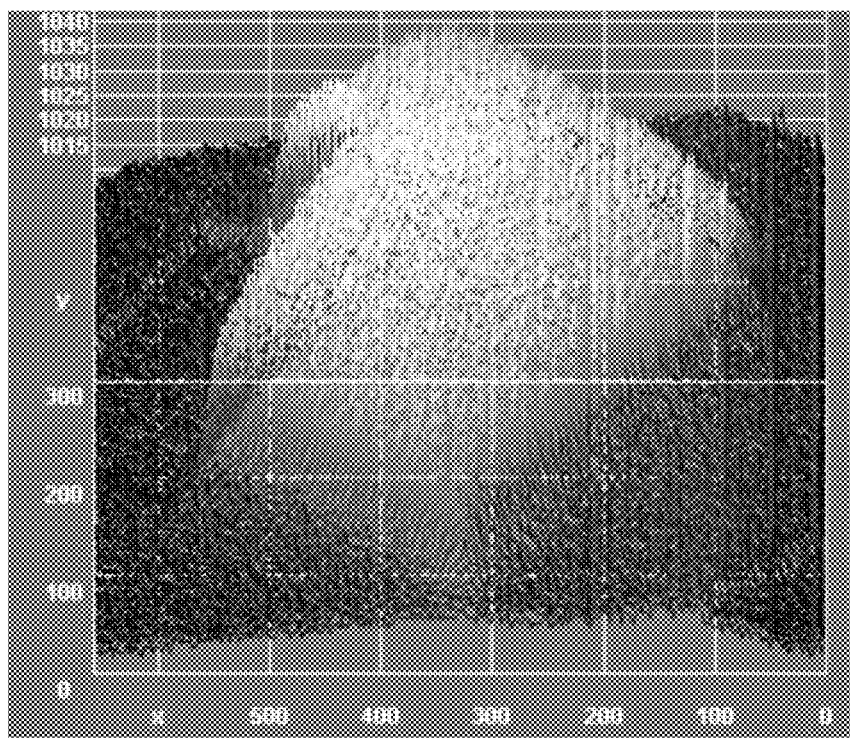

An image of a corresponding radioluminescent emission is shown in FIG. 3*a* and FIG. 3*b*, illustrating a 2D and 3D representation of radioluminescent (RL) light emitted in real time from an Al2O3:C,Mg sheet, acquired with an EMCCD camera.

It is to be noticed that the step of irradiating the object in the radiation therapy is not part of the present invention as such. The present invention relates to a dosimetry method and the dosimetry is performed by measuring a physical effect of an immobilization matrix, which does not require measurement of a physical effect in the human or animal body. Consequently, the method does not require interaction with the human or animal body and is not a method of surgery or a method of therapy.

The invention claimed is:

1. A dosimetry system for use in an irradiation system for radiology or radiotherapy, the dosimetry system comprising:
an at least two-dimensional, radioluminescent, irradiation detection surface comprising radiosensitive material, the radiosensitive material having radioluminescent properties, the at least two-dimensional, radioluminescent, irradiation detection surface being a flexible surface,
a detection system configured for detecting radioluminescent light from the at least two-dimensional detection surface upon irradiation with a radiology or radiotherapy irradiating beam,
the detection system comprising a detector being sensitive for radioluminescence and comprising a plurality of pixels for forming an image, the detection system further comprising a filter for at least partially blocking radiation from said radiology or radiotherapy irradiating beam and ambient light,
wherein the detector and the filter are positioned parallel to the radiology or radiotherapy irradiating beam.

2. The dosimetry system according to claim 1, wherein the at least two-dimensional, radioluminescent, irradiation detection surface is adapted for emitting a radioluminescent signal upon being irradiated with the radiology or radiotherapy irradiation beam, without the need for a further external stimulus.

3. The dosimetry according to claim 1, wherein the radiosensitive material has an emission decay time between 1 ns and 100 ms.

4. The dosimetry system according to claim 1, wherein the filter is adapted for blocking ambient radiation, room light and/or any contaminating light in a wavelength range between 10 and 700 nm.

5. The dosimetry system according to claim 1, wherein the filter is any of a bandpass filter, a longpass filter, a shortpass filter, a notch filter, a dichroic filter, an imaging filter or a neutral density filter.

6. The dosimetry system according to claim 1, wherein the detector is adapted for detecting light in any predetermined angle of incidence.

7. The dosimetry system according to claim 1, wherein the dosimetry system furthermore comprises a processor for processing detected radioluminescence signals and for calculating based thereon a relative or organ doses of irradiation and/or a position thereof provided to an object.

8. The dosimetry system according to claim 1, wherein the dosimetry system comprises a controller for controlling the detection of radioluminescence so that said detection of radioluminescence happens online during the radiology or radiotherapy.

9. The dosimetry system according to claim 8, wherein the controller is furthermore adapted for adjusting the radiology or radiotherapy system based on a determined dose and/or position of the detected irradiation.

10. The dosimetry system according to claim 1, wherein the radiation-sensitive material is an organic or inorganic luminescent material suitable for radioluminescence and scintillation.

11. The dosimetry system according to claim 1, wherein the radiation-sensitive material is sensitive to ionizing radiation being one or more of $\gamma$ radiation, $\beta$ radiation, $\alpha$ radiation, X-rays, protons radiation beams, hadrons radiation beams and neutrons radiation beams.

12. The dosimetry system according to claim 1, wherein the system is configured for taking into account whether radio luminescence stems from the radiosensitive material having radioluminescent properties or from the environment.

13. An irradiation system for providing radiology or radiotherapy to an object, the irradiation system comprising a dosimetry system according to claim 1.

14. The irradiation system according to claim 13, wherein the detection system for detecting radioluminescence is positioned substantially facing an irradiation source of the irradiation system.

15. The dosimetry system according to claim 1, wherein each of the plurality of pixels comprises one or more photodetection elements.

16. The dosimetry system according to claim 1, wherein the detection surface comprises a polymer material.

17. The dosimetry system according to claim 1, wherein the detection surface is shaped to cover a surface of an object.

18. The dosimetry system according to claim 1, wherein the image formed by the plurality of pixels comprises at least a two-dimensional representation of the radioluminescent light emitted from the at least two-dimensional detection surface.

19. A method for determining irradiation doses during radiology or radiotherapy for an object, the method comprising:
providing an at least two dimensional, radioluminescent, irradiation detection surface on the object, the at least two-dimensional, radioluminescent, irradiation detection surface being a flexible surface,
shaping the at least two-dimensional, radioluminescent, irradiation detection surface in accordance with the object to cover the object,
detecting radioluminescent signals from the at least two dimensional, radioluminescent irradiation detection surface using a detector being sensitive for radioluminescence and comprising a plurality of pixels for forming an image, while filtering out ambient light and radiation stemming from an irradiation beam for performing radiology or radiotherapy, the detector and the filter being positioned parallel to the radiology or radiotherapy irradiating beam, and
deriving a delivered dose and/or irradiation position on the object based on the detected radioluminescent signals.

* * * * *